United States Patent [19]
Chambers

[11] 4,235,676
[45] Nov. 25, 1980

[54] APPARATUS FOR OBTAINING HYDROCARBONS FROM RUBBER TIRES AND FROM INDUSTRIAL AND RESIDENTIAL WASTE

[75] Inventor: R. William Chambers, Tustin, Calif.

[73] Assignee: Deco Industries, Inc., Santa Ana, Calif.

[21] Appl. No.: 833,904

[22] Filed: Sep. 16, 1977

Related U.S. Application Data

[63] Continuation of Ser. No. 725,189, Sep. 21, 1976, abandoned, which is a continuation-in-part of Ser. No. 558,599, Mar. 14, 1975, abandoned, which is a continuation-in-part of Ser. No. 548,498, Feb. 10, 1975, abandoned.

[51] Int. Cl.³ .................. C09B 3/00; C10B 7/10; C10B 31/04; C10B 47/18
[52] U.S. Cl. .................. 202/118; 48/111; 48/209; 201/2.5; 201/15; 201/21; 201/25; 201/27; 201/33; 201/35; 202/114
[58] Field of Search ............ 201/2.5, 25, 32, 35, 201/21, 27, 33, 15; 202/118, 117, 113, 114; 48/111, 209; 23/290.5

[56] References Cited

U.S. PATENT DOCUMENTS

| | | | |
|---|---|---|---|
| 689,768 | 12/1901 | Wathen | 202/118 X |
| 1,972,929 | 9/1934 | Fisher | 202/118 |
| 2,072,721 | 3/1937 | Rahm | 201/33 |
| 2,422,874 | 6/1947 | Zenlea | 202/118 X |
| 2,955,988 | 10/1960 | Sebastian | 201/43 X |
| 2,973,306 | 2/1961 | Chick et al. | 201/33 |
| 3,471,369 | 10/1969 | Cox et al. | 202/118 X |
| 3,736,111 | 5/1973 | Gardner et al. | 48/209 X |
| 3,787,292 | 1/1974 | Keappler | 202/118 |
| 4,084,521 | 4/1978 | Herbold et al. | 202/118 X |

FOREIGN PATENT DOCUMENTS 2222267 11/1972 Fed. Rep. of Germany ............ 201/2.5

OTHER PUBLICATIONS

Wolfson et al. "Distructive Distillation of Scrap Tires" Bureau of Mines Report of Sep. 1969, R1 73 oc pp. 1-19.

Primary Examiner—Joseph Scovronek
Attorney, Agent, or Firm—Wills, Green & Mueth

[57] ABSTRACT

An elongated tube is maintained at a temperature of about 1100° F. throughout its length. Organic waste material such as shredded rubber automobile tires or industrial plastic waste or residential trash which preferably has metal and inorganic matter removed therefrom, is moved through the tube at a uniform rate of speed in the absence of air and/or oxygen, with the material being churned or tumbled as by means of a screw conveyor. The vapors and gases which are produced and/or liberated within the tube are quickly removed therefrom by means of a vacuum of from about four inches to about six inches of mercury, with the vapors being condensed and the gases separated therefrom. The char or residue which is a black, powdery, carbon-type material is also recovered.

12 Claims, 3 Drawing Figures

APPARATUS FOR OBTAINING HYDROCARBONS FROM RUBBER TIRES AND FROM INDUSTRIAL AND RESIDENTIAL WASTE

CROSS-REFERENCE TO RELATED APPLICATION

This application is a continuation of application Ser. No. 725,189, filed Sept. 21, 1976, now abandoned, which is a continuation-in-part of application Ser. No. 558,599, filed Mar. 14, 1975, which, in turn, is a continuation-in-part of application Ser. No. 548,498, filed Feb. 10, 1975. Applications Ser. No. 548,498 and Ser. No. 558,599 have been abandoned.

BACKGROUND AND BRIEF SUMMARY OF THE INVENTION

The present invention relates generally to the converting of organic waste materials into clean fuels and other useful products, and more particularly to a novel method and apparatus for obtaining liquid and gaseous hydrocarbons and a solid carbonaceous material from used rubber tires, from industrial waste containing relatively large amounts of plastic material, and from residential trash or waste.

At the present time, there is considerable concern in all highly industrialized countries regarding the disposal problems occasioned by the accumulation of large quantities of used automobile tires, industrial waste and residential trash . . . the latter two containing appreciable amounts of nondegradable plastic materials. In previous years, such waste materials were disposed of primarily by burning, but the enactment of air-pollution laws in most major countries now prohibit this method of disposal.

Also, at the present time, many of the so-called oil-consuming countries are concerned about the increased cost an unavailability of imported petroleum, and the dwindling supplies of natural gas.

Because of the aforementioned problems, there has been and now is an increased interest in the converting of used rubber tires, industrial plastic waste, and residential trash (including ordinary garbage) into products which can be used to produce heat or as the feed stock for various industrial processes.

The extraction of hydrocarbon materials from organic waste by the use of high temperatures has been known for many years. However, the known processes and apparatus have serious disadvantages. For example, gradual heating of the waste materials to the desired temperature results in cross-chemical reactions of the reactants and products, and the loss of useful products.

Also, the use of atmospheric and above-atmospheric pressures in the heating vessel causes the gases and vapors to slowly diffuse through the solid mass of materials and to thereby cause side reactions and cross-reactions among product species, which results in a very inefficient conversion process.

And, the prolonged heating of the gases and vapor products in the heating vessel causes recombinations, repolymerizations, and condensation of some of the products, which results in the formation of high molecular weight tars and hydrocarbons and thereby reduces the yield of the useful products. In addition, some of these high molecular weight tars and hydrocarbons form surface coatings on the feed materials and thereby block the release of new gases and vapors from the unreacted feed materials.

With the aforementioned problems and the limitations and deficiencies of known apparatus and methods in mind, it is a general object of the present invention to provide a novel method and apparatus for converting organic waste materials into clean fuels and other useful hydrocarbon products. More particularly, one of the primary objects is to provide a novel method and apparatus for obtaining useful hydrocarbon products from used rubber tires, from industrial plastic waste, and from residential trash.

Another object is to provide a novel method and apparatus for obtaining a hydrocarbon feed stock for petrochemical plants, from used rubber tires and from waste plastic materials.

Yet another object of the present invention is to provide a simple, continuous, and relatively inexpensive process for obtaining pipeline quality gas and oil from used rubber tires, from waste plastic materials, and from residential trash.

A further object is to provide a novel method and apparatus for obtaining from used rubber tires and waste plastic materials, a carbonaceous char which can be readily converted to activated carbon, or used as a smokeless fuel, or used as an asphalt and chemical filler.

I have discovered that the above objects and advantages are achieved by continuously moving a mass of shredded rubber tires, waste plastic materials, or residential trash (including ordinary garbage) through an elongated tubular member maintained at a temperature of between about 800° F. and 1500° F. throughout its length, in the absence of air and/or oxygen, with the material being turned or stirred as it passes through the tubular member, and with the gases and vapors being removed from adjacent the outlet end of said member by means of a vacuum of from about four inches to about six inches of mercury. To increase the production rate, a plurality of such tubular members can be provided in the same heating vessel in a side-by-side relationship, and/or the diameter of the tubular members can be increased in size with accompanying provisions for maintaining a substantially constant temperature throughout the mass of material being processed.

Based upon present information, it appears that the relatively high temperature adjacent the inlet of the tubular member (and throughout its length) and the constant stirring or turning of the material so as to continuously expose it to the heated surface or surfaces of the tubular member, causes the gases and vapors to literally "explode" from the material, and the relatively high vacuum throughout the length of the tubular member causes the vapors and gases to be quickly withdrawn before they can repolymerize or condense onto the feed material.

DESCRIPTION OF THE PREFERRED EMBODIMENTS

Figure 1:
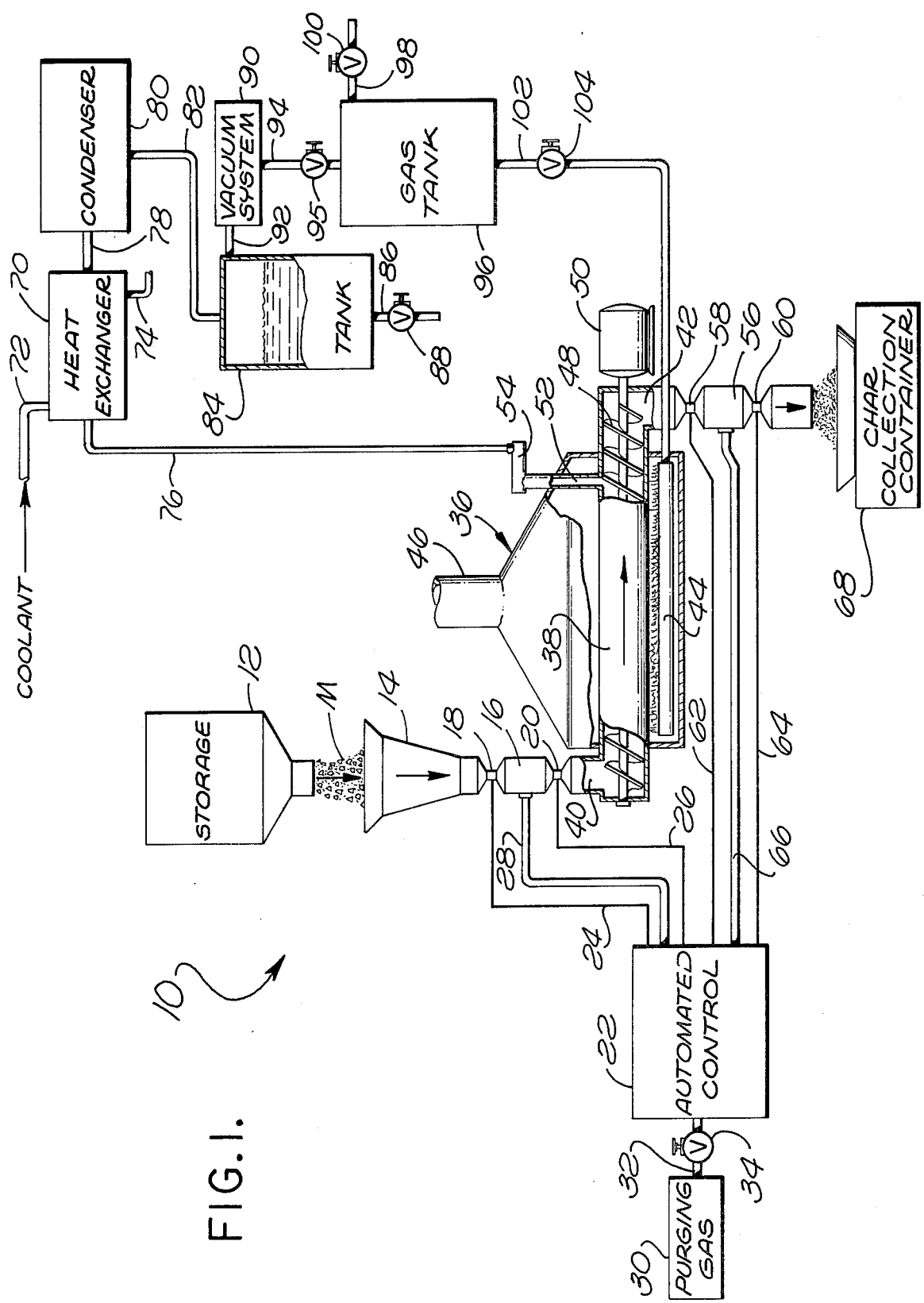
FIG. 1 is a schematic elevational view, partially in cross-section and somewhat in the nature of a flow diagram, illustrating one form of apparatus for practicing the teachings of the present invention.

Referring to the drawings more particularly by reference numerals, and specifically to FIG. 1, the number 10 indicates one form of apparatus for practicing the teachings of the present invention, which includes a storage bin 12 from which the feed material "M" can be discharged into a hopper 14.

Positioned beneath the hopper 14 is an air-tight inlet chamber 16 which has an inlet 18 for admitting a charge of material into the chamber, and an outlet 20 for discharging the material therefrom. Each inlet and outlet is provided with a sliding door movable between an open position and a closed position, responsive to signals from an automated control 22 transmitted through control lines 24 and 26, respectively. The specific means for controlling the movement of said doors is a matter of choice and can be either electrical, hydraulic or pneumatic.

Extending between the inlet chamber 16 and the control 22, is a first purging conduit 28, which can be selectively placed in communication with a container 30 of purging gas such as nitrogen, through a pipe 32 which contains a valve 34.

The reactor system includes an insulated heating vessel 36 through which extends an elongated pipe or tube 38 and which contains an inlet 40 and an outlet 42. I have used a 6 inch diameter stainless steel tube in the prototype apparatus.

A source of heat such as a gas burner 44 is provided in the heating vessel 36 beneath the tube 38, and a vent or chimney 46 is provided at the top of the vessel for the discharge of the products of combustion therefrom.

A screw conveyor 48, which is driven by an electric motor 50 extends through the tube 38 from adjacent the inlet 40 to adjacent the outlet 42, for moving the material through the tube at a uniform rate of speed with a churning or stirring movement, whereby to continuously expose all of the chunks or particles of material to the heat at the surface of the tube 38.

A product outlet pipe 52 is in communication with a connector pipe 54 and with the interior of the tube 38 adjacent to its outlet end, the outlet pipe being within the heating vessel so as to be exposed to the heat therein. Stating it somewhat differently, the product outlet pipe 52 should be maintained at a relatively high temperature so that the hydrocarbon products being removed from the tube 38 as gases or vapors remain in such state, as will be described more fully hereinafter.

Adjacent the outlet 42 of the tube 38 is an air-tight outlet chamber 56 which is similar in construction to the inlet chamber 16 previously described. Thus, it contains an inlet 58 and an outlet 60, each of which is provided with a sliding door movable between an open position and a closed position responsive to the automated control 22 which is in communication therewith through control lines 62 and 64, respectively.

A second purging conduit 66 extends between the outlet chamber 56 and the automated control 22 and is in selective communication with the container 30 of purging gas.

Positioned beneath the outlet chamber 56 is a char collection container 68.

The product recovery system includes a heat exchanger 70 which contains a coolant inlet 72 and a coolant outlet 74 for causing cooling fluid to pass therethrough. The heat exchanger 70 also includes a product inlet pipe 76 which is connected to the connector pipe 54, and a product outlet pipe 78 which is connected to the inlet of a condenser 80. The outlet of the condenser is connected through a pipe 82 with the inlet of a liquid storage tank 84 which has a drain pipe 86 at the bottom thereof, the drain pipe 86 being provided with a valve 88 for selectively draining liquid products therefrom.

A vacuum system 90 has the inlet thereof connected to the upper portion of the liquid storage tank through a pipe 92, and the outlet of the vacuum system is connected through a pipe 94 and valve 95 with the inlet of a gas tank 96 which has a discharge pipe 98 adjacent the upper end thereof, the discharge pipe being provided with a discharge valve 100.

Connected to the bottom of the gas tank 96 is a fuel pipe 102 which has a valve 104 positioned therein, and which pipe is connected to the gas burner 44 positioned in the bottom portion of the heating vessel 36 beneath the tubular member 38.

In operation, the feed material "M" . . . which can be shredded rubber tires or crushed industrial plastic waste or residential trash which preferably has metal and other organic materials removed therefrom as will be described more fully hereinafter . . . is discharged from the storage bin 12 and into the hopper 14.

The automated control 22 is adjusted so that with the outlet 20 of the inlet chamber 16 in the closed position, the inlet 18 is opened to permit a measured charge of material to enter into the inlet chamber 16. Thereafter, the inlet 18 is closed and a charge of purging gas such as nitrogen is admitted into the inlet chamber 16 through the conduit 28, whereby to displace all of the air from the inlet chamber 16.

With the inlet 18 closed, the outlet 20 of the chamber 16 is opened, whereby the material "M" passes through the inlet 40 of the tube 38 and is carried through the tube by means of the screw conveyor 48.

The opening and closing of the inlet 18 and outlet 20 and the purging of the inlet chamber 16 with a gas such as nitrogen, occurs at relatively short intervals of time, whereby there is practically a continuous flow of material into the inlet end of the tube 38.

The char which remains after the vapors and gases are removed from the material, passes through the outlet 42 of the tube and into the outlet chamber 56. The outlet chamber 56 functions in a manner similar to the inlet chamber 16, with the outlet 60 being closed and the inlet 58 being opened to permit a charge of char to pass into the outlet chamber, with the inlet 58 then being closed and the outlet 60 opened to discharge the char into the container 68. The outlet 60 is then closed, and with both the inlet and outlet in the closed position, purging gas is admitted into the outlet chamber through the conduit 66, so as to purge any air from the outlet chamber. Thereafter, the inlet 58 is opened to permit another charge of char to enter the outlet chamber, and the sequence is again repeated to discharge the char into the container 68. As mentioned hereinabove, the opening and closing of the inlet 58 and the outlet 60, and the purging of the outlet chamber 56, occur at relatively short intervals of time, whereby there is substantially a continuous flow of char from the outlet 42 of the tube 38 and into the container 68.

As will be explained more fully hereinafter, I have learned that the temperature in the heating vessel 36 should be at least 800° F., and preferably as high as 1500° F. depending upon the proportions of gases desired. Also, that the vacuum within the tube 38 should be from about four inches to about six inches of mercury. The diameter of the tube 38 and the speed at which the material is moved through the tube 38 by the conveyor 48 should be such that the temperature of the material being processed reaches the mean temperature in the retort within a few feet of the side of the retort adjacent the inlet 40. Thus, it appears that the sudden increase in the temperature of the material to no less than about 800° F. by the time it has moved a few feet into the vessel, causes a sudden "shock" heating which, together with the vacuum in the tube, causes the vapors and gases to literally "explode" from the chunks or particles and the vacuum causes them to be carried away from the churning, turning mass of material before they can repolymerize or condense upon the remaining solid material.

Turning to the operation of the product recovery system, the gases and vapors which are produced and/or liberated in the tubular member 38, pass through the product outlet pipe 52 and the pipes 54 and 76, and through the heat exchanger 70, whereby the vapors are condensed and the gases are cooled.

From the condensor 80, the gases and liquid pass through the pipe 82 and into the upper end of the tank 84, with the water and oil remaining in the tank and the gases passing through the pipe 92, the vacuum system 90, and the pipe 94 . . . into the gas tank 96.

The fuel gas thus produced can flow through the pipe 102 to the burner 44 and be used to heat the vessel 36, or can be discharged through the outlet pipe 98 and valve 100 for other purposes.

For initially starting the system, the valve 95 is closed and commercial fuel gas is admitted into the gas tank 96 through the pipe 98 and valve 100. However, after the system is operating and fuel gas is being produced in sufficient quantities, the valve 95 is opened and the system becomes self-sustaining insofar as the fuel gas is concerned. And, when it is necessary or desirable to shut-down the system, valves 95, 100 and 104 can be closed, thereby maintaining a "start-up" supply of fuel gas in the tank 96. Obviously, if at any time not enough fuel gas is being produced in the system to maintain the heating vessel 36 at the proper temperature, additional commercial fuel gas can be admitted into the gas tank through the pipe 98 and the valve 100.

As mentioned above, various feed materials can be processed using the method and apparatus of the present invention, including shredded rubber automobile tires, industrial plastic waste materials, and residential trash (including ordinary garbage).

EXAMPLE NO. 1

Although residential trash from which metal and like inorganic materials have been removed varies from city to city and from one section of a city to another section thereof, a typical physical composition of such residential trash, which often contains relatively large amounts of plastic material, is as follows, by weight:

| Volatile Matter | 75% |
|---|---|
| Fixed Carbon | 11% |
| Ash | 14% |

The chemical composition of such "typical" dry residential trash, is as follows, by weight:

| Component | Percentage |
|---|---|
| Hydrogen | 5.5 |
| Carbon | 46.0 |
| Nitrogen | 1.8 |
| Oxygen | 33.2 |
| Sulphur | 0.5 |
| Ash | 16.0 |

Using the apparatus previously described, and with a temperature of the heating vessel at about 1100° F. and with a vacuum between about four inches and about six inches of mercury, the following listed yield was obtained, wherein the percentage of yield is by weight of dry feed material.

| Product | Percent | Amount |
|---|---|---|
| Oil | 40 | 2.7 bbl/ton |
| Gas | 32 | 8,000 scf/ton |
| Char | 16 | 320 pounds/ton |
| Water | 12 | 240 pounds/ton |

The char or solid residue was a black, powdery material, similar in appearance to amorphous carbon, and consisted primarily of fixed carbon and ash.

The gas which was produced had the following composition, by volume.

| Product | Percentage |
|---|---|
| Hydrogen | 20 |
| Nitrogen | 10 |
| Methane | 21 |
| Carbon Monoxide | 2 |
| Carbon Dioxide | 6 |
| Ethane | 10 |
| Ethylene | 3 |
| Propane and Higher Hydrocarbons | 26 |

EFFECT OF TEMPERATURE ON GAS PRODUCED

By changing the temperature of the heating vessel from 1100° F. to either 800° F. or 1500° F., the amounts of the various gases which are produced from residential trash can be varied to an appreciable extent, as shown by the following table in which the gas composition is in percent by volume:

| Product | Ex. 2 800° F. | Ex. 1 1100° F. | Ex. 3 1500° F. |
|---|---|---|---|
| Hydrogen | 10 | 20 | 35 |
| Nitrogen | 12 | 10 | 8 |
| Methane | 16 | 21 | 18 |
| Carbon Monoxide | 8 | 2 | 2 |
| Carbon Dioxide | 18 | 6 | 7 |
| Ethane | 8 | 10 | 4 |
| Ethylene | 2 | 3 | 4 |
| Propane and higher Hydrocarbons | 18 | 26 | 20 |

EXAMPLES NO. 4 AND NO. 5

As previously mentioned, another type of waste material which can be processed using the teachings of the present invention, to provide oil, a carbonaceous char, and high quality fuel gas, comprises waste plastic materials obtained from manufacturing processes.

Two different mixtures of polypropylene and polystyrene, processed at 1100° F. and with a vacuum between about four inches and six inches of mercury, produced the following percentages of gases:

| Product | Ex. No. 4 Percentage | Ex. No. 5 Percentage |
| --- | --- | --- |
| Nitrogen | 12.2 | 11.4 |
| Carbon Monoxide | 1.3 | 1.0 |
| Carbon Dioxide | 3.8 | 3.5 |
| Methane | 8.3 | 7.0 |
| Ethane | 9.7 | 9.5 |
| Propane | 33.6 | 39.7 |
| Butane | 10.5 | 11.1 |
| Hydrogen | 7.4 | 5.0 |

The amount of gas produced in each of these examples was about 1,500 cubic feet per ton of starting material, and the oil was about 83 percent, by weight, and the char was about 7 percent, by weight, of the starting material.

EXAMPLE NO. 6

Another starting material, which is in abundant supply in many industrial countries, including the United States, Japan, and West Germany, and which presents a serious disposal problem, is used rubber automobile tires.

Such rubber tires which had the metal removed and which were shredded into small pieces approximately three-fourths of an inch in length and about one fourth inch in thickness, were processed using the apparatus previously described, at a temperature of about 1100° F. and with a vacuum between about four inches and about six inches of mercury.

The products recovered, per ton of starting material, were as follows:

| | | |
| --- | --- | --- |
| Light oil | 3 barrels | |
| Gas | 1,900 cubic feet | |
| Char | 700 pounds | |

If it is desired to produce more gas and less oil and char, the operating temperature should be increased above 1100° F.

The char which was produced in a powdery carbon-black type of material with a heating value of about 19,500 Btu per pound.

The gas which was produced had the following composition, by volume:

| Product | Percentage |
| --- | --- |
| Hydrogen | 6 |
| Nitrogen | 17 |
| Carbon Monoxide | 4 |
| Methane | 20 |
| Carbon Dioxide | 5 |
| Ethane | 7 |
| Propane and Higher Hydrocarbons | 28 |

Because this gas obtained from used rubber tires contains in excess of 55%, by volume, of light molecular weight hydrocarbons, it has a very high heating value, comparable to natural gas.

The yield of oil, by weight, according to the boiling point range of the oil, was as follows:

| Boiling Point Range(°C.) | Yield (Wt., %) |
| --- | --- |
| -97 | 7.0 |
| 97-150 | 9.9 |
| 150-190 | 8.1 |
| 190-265 | 17.8 |
| 265-375 | 31.0 |
| Residue | 26.0 |

ALTERNATIVE FORM OF APPARATUS

As mentioned above, I have used a six inch diameter stainless steel pipe as the tubular member 38, in achieving the aforementioned results, with the temperature gradient between the outer surface of the pipe and the center of the pipe being about 10° F.

If it is desired to increase the capacity of the apparatus, additional pipes or tubular members can be placed in the heating vessel in a side-by-side relationship, and/or the diameter of the tubular members can be increased.

Figure 2:
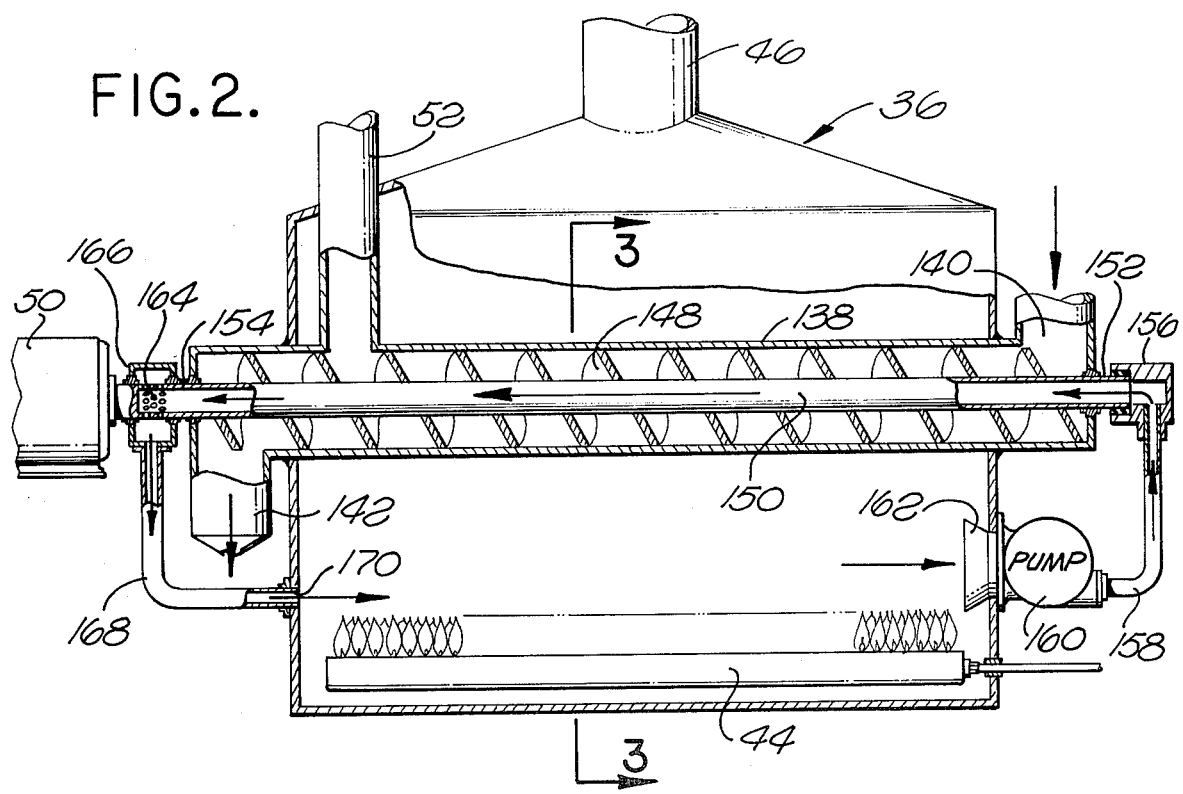
FIG. 2 is an enlarged elevational view, partially in cross-section, showing an alternative form of heating vessel containing a plurality of tubular members of increased diameter, in order to increase the capacity of the system.
Figure 3:
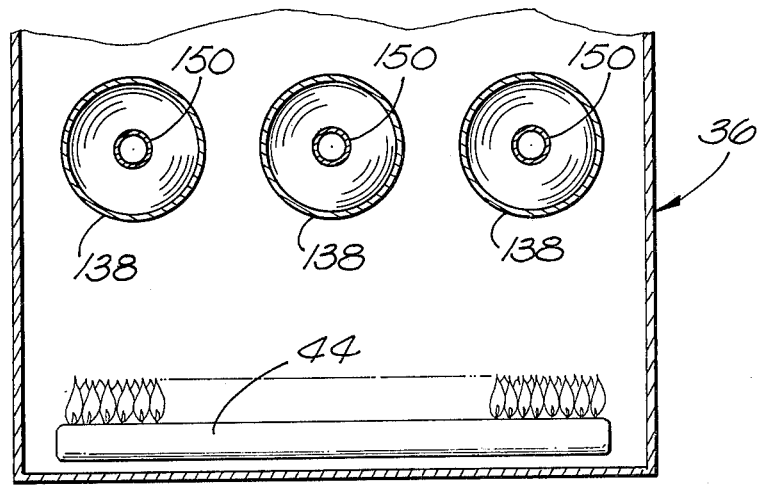
FIG. 3 is a vertical, sectional view taken on the line 3—3 in FIG. 2.

Referring to FIGS. 2 and 3 which show one such alternative form of apparatus, the single tubular member 38 is replaced with three tubular members 138 of increased diameter, which are positioned in a spaced apart, side-by-side relationship above the same gas burner 44. Each of the tubular members 138 is provided with the same type of inlet 140 and outlet 142 as previously described, and the controlled inlet and outlet chambers for excluding air, are the same.

However, because of the increased diameter of the tubular members and the desirability of maintaining approximately a 10° F. gradient between the outer surface of the tube and the center thereof, each of the tubular members is provided with a hollow shaft through which hot gases can be circulated.

Thus, each screw conveyor 148 has a hollow shaft 150 with an inlet end 152 and an outlet end 154. The inlet end 152 extends beyond the tubular member 138 and is in communication with and is rotatably received in a hollow, gas-tight fitting 156, the interior of which fitting is in communication with a pipe 158, which, in turn, is connected to a pump 160 which has an inlet 162 in communication with the interior of the heating vessel 36.

The outlet end 154 of the hollow shaft is connected to the electric motor 50, and between the motor and the end of the tubular member 138 there is a plurality of openings of vents 164 to permit the passage of hot gases.

Surrounding the vented end portion of the hollow shaft 150 in relative rotational relationship therewith is a gas-type housing 166, the interior of which housing is in communication with a pipe 168 which has its outlet in communication with an opening 170 provided in the wall of the heating vessel 36.

Thus, hot gases which enter the inlet 162 of the pump 160, flow through the pipe 158 and the fitting 156, into the interior of the hollow shaft 150 so as to transmit heat to the center of the mass being conveyed through the tubular member 138. The gases exit from the hollow shaft through the openings 164, and then flow through the pipe 168 and return to the interior of the heating vessel 36.

It is to be understood that other means can be employed for heating the hollow shaft 150 in order to obtain the same result, as for example, an electrical resistance coil can be positioned in the hollow center of the shaft.

Thus, it is apparent that there have been provided a novel method and alternative forms of apparatus, which fulfill all of the objects and advantages sought therefor.

I claim:

1. Apparatus for obtaining hydrocarbon products from organic feed material, comprising:
    an insulated heating chamber;
    at least one stationary elongated tubular member having an inlet and an outlet, positioned in said chamber;
    means for heating the tubular member to at least about 800° F.;
    means including a screw conveyor having a hollow shaft, which rotates relative to the tubular member for continuously moving feed material through the tubular member from the inlet to the outlet thereof at a substantially constant rate of speed;
    means for heating the interior of the hollow shaft;
    means for preventing the introduction of air into the tubular member during the movement of feed material therethrough; and
    means for producing a vacuum within said tubular member and for continuously removing vapors and gases therefrom.

2. Apparatus according to claim 1, in which the heating means for the hollow shaft comprises means for directing hot gases through the interior and said hollow shaft.

3. Apparatus according to claim 1, in which the heating means for the hollow shaft comprises means for directing hot gases through the interior of the hollow shaft in the same direction as the flow of the feed material through the tubular member.

4. Apparatus for obtaining hydrocarbon products from organic feed materials, comprising:
    an elongated tubular member having an inlet and an outlet adjacent opposite ends thereof;
    means including a shaft mounted within said tubular member for moving feed material from the inlet to the outlet thereof;
    means for heating the interior of the tubular member to at least 800° F., including a passageway through said shaft and means for moving a heat-transmitting substance through said passageway;
    means for preventing the entrance of air into the tubular member during the movement of feed material therethrough;
    means for producing a vacuum within said tubular member and for continuously removing vapors and gases therefrom adjacent said outlet;
    means for cooling the removed gases and condensing the vapors to a liquid; and
    means for separating the gases from the liquid.

5. Apparatus according to claim 4, in which the means for moving feed material through the tubular member includes a screw conveyor mounted for rotational movement relative to the tubular member.

6. Apparatus according to claim 5, in which the tubular member is stationary and the screw conveyor rotates.

7. Apparatus according to claim 5, in which the screw conveyor extends from adjacent the inlet to adjacent the outlet and moves the feed material through the tubular member at a substantially constant rate of speed.

8. Apparatus according to claim 4, in which the heat-transmitting substance is directed through the passageway from adjacent the inlet to adjacent the outlet of the tubular member.

9. Apparatus according to claim 4, in which the means for moving a heat-transmitting substance includes a pump for moving fluids through said passageway.

10. Apparatus according to claim 4, which further includes means for recovering the residue from the feed material after the gases and vapors have been removed therefrom.

11. Apparatus according to claim 4 in which the means for heating the interior of the chamber includes means for burning hydrocarbon products removed from the tubular member.

12. Apparatus according to claim 4 in which means are provided for heating the heat transmitting substance and which includes means for burning hydrocarbon products removed from the tubular member.

* * * * *